United States Patent [19]

Scala, Jr.

[11] 4,322,545

[45] Mar. 30, 1982

[54] BENZOIC ACID ESTERS

[75] Inventor: Thomas L. Scala, Jr., West Milford, N.J.

[73] Assignee: Finetex, Inc., Elmwood Park, N.J.

[21] Appl. No.: 252,794

[22] Filed: Apr. 13, 1981

Related U.S. Application Data

[63] Continuation-in-part of Ser. No. 741,071, Sep. 14, 1979, Pat. No. 4,275,222, which is a continuation-in-part of Ser. No. 949,630, Oct. 10, 1978, abandoned.

[51] Int. Cl.³ .......................................... C07C 69/76
[52] U.S. Cl. ...................................... 560/103; 424/59; 424/60; 424/308
[58] Field of Search ..................... 560/103; 424/59, 60, 424/308

[56] References Cited

U.S. PATENT DOCUMENTS 2,428,450 10/1947 Eitelmon ............................ 560/103
3,506,704 3/1970 Miller ................................. 560/103

FOREIGN PATENT DOCUMENTS 130438 11/1946 Australia ............................ 560/103
1943453 10/1973 Fed. Rep. of Germany ...... 560/103

OTHER PUBLICATIONS

Chemical Abstract 390102 vol. 66, 1967.

Meyerson et al. JACS 95:18 Sep. 5, 1973 pp. 6056–6067.

*Primary Examiner*—Paul J. Killos
*Attorney, Agent, or Firm*—Weingram & Klauber

[57] ABSTRACT

A substantially pure benzoic acid ester of a mixture of alcohols. The mixture of alcohols consists essentially of (A) at least one $C_{12}$ or $C_{14}$ primary alcohol and (B) at least one $C_{13}$ or $C_{15}$ primary alcohol. The weight ratio of the even carbon number alcohols (A) to the odd carbon number alcohols (B) is from about 0.25:1 to about 4:1, preferably from about 0.5:1 to about 3:1. At least 70% by weight of each alcohol is linear and substantially all of the remainder of each alcohol is branched at the two carbon position. The compositions of this invention have unique properties in that they are substantially non-greasy, lack oiliness and greasiness, have low cloud points and pour points, have a bland odor, low toxicity, and are stable. The properties make such compositions useful as a vehicle or carrier, emollient or solubilizer for toiletry and cosmetic formulations, e.g., hair cream, hand cleaner, bath oil, suntan oil, brilliantine, anti-perspirants, perfumes and colognes, cold creams, electric pre-shave, eye and throat oil, fingernail polish, topical pharmaceutical ointments, lipsticks, stick rouge, skin lotions and creams, skin moisturizers, cleansing creams and after bath splash and lotions.

6 Claims, No Drawings

# BENZOIC ACID ESTERS

RELATED APPLICATIONS

This application is a continuation-in-part of copending application Ser. No. 74,071, filed Sept. 14, 1979, U.S. Pat. No. 4,275,222 which is a continuation-in-part of application Ser. No. 949,630, filed Oct. 10, 1978, now abandoned, both of which are entitled "Improved Ester Compositions". Some of the novel uses of the claimed compositions in this application are described and claimed in an approximately concurrently filed U.S. application, entitled "Skin Care Compositions", which is a continuation-in-part of U.S. Ser. No. 18,250 filed on Mar. 7, 1979 U.S. Pat. No. 4,278,655 and entitled, "Anti-Perspirant Composition". The latter is a continuation-in-part of U.S. Ser. No. 100,917, filed Dec. 6, 1979, U.S. Pat. No. 4,293,544 entitled "Fluid and Semi-Fluid Compositions Including Benzoate Esters". All of these aforementioned applications are assigned to the assignee of this application. The entire disclosures of all of these applications are incorporated herein by reference.

BACKGROUND OF INVENTION

1. Field of the Invention

This invention relates generally to a novel ester composition, and more particularly to a benzoic acid ester of a mixture of $C_{12}$ through $C_{15}$ alcohols. The compositions are particularly useful as a carrier or vehicle or an emollient and solubilizer for cosmetic and toiletry formulations.

2. Prior Art

Mixtures of alcohols within the $C_{12}$ through $C_{15}$ range are well-known in the art. Particularly unique alcohols are the $C_{12}$ through $C_{15}$ primary alcohols sold under the trademark NEODOL by Shell Chemical Company, Industrial Chemicals Division. These alcohols are generally linear primary alcohols which are produced in a substantially pure condition. These alcohols can be made into derivatives such as ethoxylates, ethoxysulfates and sulfates. The NEODOL alcohols and the aforementioned derivatives are generally used in the detergent industry, for textile and oil processing, specialty cleaners and personal care products.

The NEODOL alcohols are characterized in that they are linear primary alcohols having even and odd numbered carbon atoms in the $C_{12}$ to $C_{15}$ detergent range. Previously, alcohols derived from natural substances were only even numbered. The NEODOL alcohols are unique in that they contain both odd and even numbered carbon atoms. The odd numbered alcohol contributes significantly to the performance of certain derivatives of these alcohols.

As previously mentioned, there are known derivatives of such $C_{12}$ through $C_{15}$ alcohols, for example, the ethoxylates, ethoxysulfates, and sulfates. To applicant's knowledge however, there are no known benzoic acid ester derivatives of the $C_{12}$ through $C_{15}$ NEODOL alcohols.

U.S. Pat. No. 3,506,704 to Miller et al describes a process for the production of organic esters produced in a liquid phase reaction of 1-hydrocarbyl bromides with hydrocarbonic acids. preferred embodiment of Miller et al, benzoic acid and n-dodecyl bromide ($C_{12}$) are reacted at an elevated temperature in the presence of lithium benzoate. Hydrogen bromide is evolved in the course of the reaction and attempts are made to remove the hydrogen bromide from the reaction zone. Miller et al states that such hydrogen bromide is well-known to cause extensive discoloration and deletorious effects.

In Table III, Run 25 of Miller et al, benzoic acid is reacted with what is apparently a mixture of bromides in the $C_{11}$ to $C_{15}$ range. These mixtures are obtained from cracked wax alpha olefins which originate from petroleum, and thus are highly contaminated impure products. The Miller et al esters, as mentioned, are formed by a severe acid-bromide reaction and result in products which are invariably contaminated or discolored by hydrogen bromide. There is no disclosure in Miller et al of any particular mixture of odd and even ($C_n$) benzoic acid esters, much less is there any disclosure relating to specific proportions of such odd and even ($C_n$) benzoic acid esters.

Further, certain linear alkyl benzoates are known in the art, e.g. lauryl benzoate, stearyl benzoate. None of these benzoates have the unique properties of the ester compositions described and claimed herein.

OBJECTS AND SUMMARY OF THE INVENTION

It is an object of this invention to provide a novel ester composition having unique properties which make it uniquely suitable as a vehicle or carrier in toiletry and cosmetic compositions.

It is a further object of this invention to provide a substantially pure benzoic acid ester of a mixture of alcohols, said ester product having unexpected properties not taught or suggested by the prior art, which make the composition uniquely suitable for broad application in toiletry and cosmetic compositions.

The foregoing objects and other objects are attained by a substantially pure benzoic acid ester of a mixture of alcohols. The mixture of alcohols consists essentially of:

(A) at least one $C_{12}$ or $C_{14}$ primary alcohol; and
(B) at least one $C_{13}$ or $C_{15}$ primary alcohol.

The weight ratio of even carbon number alcohols (A) to odd carbon number alcohols (B) in the mixture is from about 0.25:1 to about 4:1, preferably from about 0.5:1 to about 3:1. At least 70% by weight of each alcohol is linear and substantially all of the remainder of each alcohol is branched at the 2-carbon position.

Preferably, such a composition consists essentially of $C_{12}$, $C_{13}$, $C_{14}$ and $C_{15}$ alcohols, however, other mixtures are contemplated.

DETAILED DESCRIPTION OF THE INVENTION

The compositions of this invention are produced by reacting benzoic acid with the mixture of alcohols. Preferably, methane sulfonic acid is used as a catalyst. It is contemplated, however, that any method of producing such benzoic acid esters can be utilized as long as such method does not interfere with their intended use, particularly in the cosmetic and toiletry field. In particular, the process for producing the esters should permit them to be purified to a substantially pure condition. By the use of the term "substantially pure," it is meant that the compositions do not contain impurities which interfere with their intended use, particularly as carriers or vehicles in toiletry and cosmetic formulations.

The alcohol precursors used in preparing the benzoic acid esters of this invention are a mixture of alcohols. As previously stated, the mixture consists essentially of:

(A) at least one $C_{12}$ or $C_{14}$ primary alcohol; and
(B) at least one $C_{13}$ or $C_{15}$ primary alcohol.

It is believed that contributing to the uniqueness of the benzoic acid esters of this invention are the fact that the alcohols used in producing such an ester are a mixture of both odd and even alcohols. Comparative testing appears to indicate that such a mixture is required in order to obtain an ester having the unique properties of the claimed composition.

Particularly preferred mixtures of alcohols are the $C_{12}$ through $C_{15}$ mixtures, the $C_{12}$ and $C_{13}$ mixture and the $C_{14}$ and $C_{15}$ mixtures.

The alcohol mixture has a weight ratio of even carbon number alcohols (A) to odd carbon number alcohols (B) of from about 0.25:1 to about 4:1. The preferred range is from about 0.5:1 to about 3:1. The preferred NEODOL 25 alcohol specifically described in this application has a weight ratio of about 0.9; the NEODOL 23 has a weight ratio of about 0.47; and the NEODOL 45 has a weight ratio of about 2.125. It is believed that if one goes substantially below a weight ratio of about 0.25:1, or substantially above a weight ratio of about 4:1, the unique properties of the benzoic acid ester compositions of this invention will be substantially reduced.

As indicated previously, the alcohol precursors used in preparing the products of this invention include primary alcohols having a proportion of branching at the two-carbon position. Generally, such primary alcohols are represented by the formula ROH, where R is a primary alkyl group of from 12 to 15 carbon atoms. The alcohol in the mixture of alcohols may be represented by the formula:

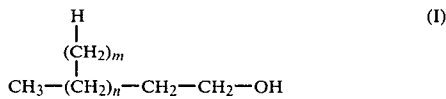

(I)

wherein m is a whole number from 0 to 6 inclusive, and n is a whole number from 6 to 12 inclusive, such that $m+n+3=12, 13, 14$ or $15$. In such alcohols, e.g., the NEODOL alcohols, at least 70% by weight of the alcohol of each specific chain length is linear (i.e., $m=0$). Branching, if it exists, comprises about 50% methyl ($m=1$) and smaller amounts of ethyl ($m=2$), propyl ($m=3$), butyl ($m=4$), amyl ($m=5$), and hexyl ($m=6$) group branching.

Alcohols of the foregoing type may be made by the direct hydroformylation of olefins to give alcohol, for example, see Kirk-Othmer, Encyclopedia of Chemical Technology, 3d Edition, Vol. 1, p. 751 and references incorporated therein.

It is believed, however, that the unique properties of the benzoic acid ester compositions of this invention are due to the high normal or linear alcohol content of the precursor alcohols, i.e., at least 70% by weight of the alcohol, combined with the mixture of odd and even numbered carbom atoms. Such unique alcohols appear to be produced only by the "Shell process" which produces $C_{12}$-$C_{15}$, i.e., "coconut" range, primary alcohols, and sold under the trademark "NEODOL." Applicant, however, does not exclude from his invention the use of alcohols made by other processes. The NEODOL alcohols are sold by Shell Chemical Co., Houston, Tex. These alcohols are also manufactured in the United Kingdom and Japan using the same technology and are marketed outside of North America by Shell International Co., London, under the name DEBANOL.

With respect to specific mixtures of alcohols used to make the benzoic acid ester compositions of this invention, it is highly preferred that the alcohol mixture contain a mixture of $C_{12}$ through $C_{15}$ primary alcohols.

It has also been found that a mixture consisting essentially of $C_{12}$ and $C_{13}$ alcohols and a mixture of $C_{14}$ and $C_{15}$ alcohols may also be used to produce an ester having most of the unique properties which make such composition useful.

More specifically, NEODOL 25 alcohol is the highly preferred mixture of alcohols. A typical analysis consists essentially of $C_{12}$—29.4%; $C_{13}$—36.7%; $C_{14}$—18.3%; and $C_{15}$—15.5%. such a composition has a weight ratio of even carbon numbered alcohols to odd carbon numbered alcohols of about 0.913. A preferred range consists essentially of a mixture of:

| Alcohol | Preferred Weight (%) | Highly Preferred Weight (%) |
|---|---|---|
| $C_{12}$ | 13–31 | 23–31 |
| $C_{13}$ | 28–44 | 32–44 |
| $C_{14}$ | 17–40 | 17–23 |
| $C_{15}$ | 12–19 | 12–18 |

Less preferred, although still contemplated by this invention, are the NEODOL 23 alcohol and the NEODOL 45 alcohol, and mixtures thereof, for example, a 1:1 weight ratio of NEODOL 23 to NEODOL 45. Typically, the NEODOL 23 alcohol has 32% $C_{12}$ and 68% $C_{13}$ alcohol, with a weight ratio of $C_{12}$ to $C_{13}$ of about 0.470. The NEODOL 45 alcohol has 68% $C_{14}$ alcohol and 32% $C_{15}$ alcohol, with a weight ratio of even carbon numbered atoms to odd carbon numbered atoms of about 2.125. The mixture of NEODOL 23/45 at a 1:1 weight ratio typically has in it $C_{12}$—16%; $C_{13}$—34%; $C_{14}$—34%; $C_{15}$—16%.

The benzoic acid ester compositions of this invention have unique properties particularly suited for use as a vehicle and a carrier in toiletry and cosmetic compositions. One particular use is in an antiperspirant composition, see, for example, the aforementioned U.S. Ser. No. 018,250, now U.S. Pat. No. 4,278,655; and the use of such compositions in sunscreening compositions, see for example, the aforementioned U.S. Ser. No. 100,917 to Elmi, now U.S. Pat. No. 4,293,544.

The benzoic acid ester compositions of this invention are characterized by the following properties:
 1. Lack of greasiness;
 2. Lack of oiliness;
 3. Low cloud point and pour point;
 4. Bland odor;
 5. Gel formation—ability to form gels with suspending agents;
 6. Low toxicity;
 7. Emulsifying properties.

The foregoing properties make the compositions of this invention particularly useful in toiletry and cosmetic products, e.g., hair creams, hand cleaners, bath oils, suntan oils, hair brilliantines, antiperspirants, perfumes, colognes, sunscreen butters, cold creams, electric preshaves, eye and throat oils, skin gels, fingernail polishes, pharmaceutical ointments, deodorants, lotions, moisturizers, facial cleansers, and after bath splashes and lotions.

The following are non-limiting examples of processes for producing the compositions of this invention, properties of the compositions and uses of the compositions in specific toiletry and cosmetic products.

BENZOIC ACID ESTER COMPOSITIONS

EXAMPLE 1

A mixture of 227.7 parts (1.1 mol) of the aforedescribed NEODOL 25, alcohol, 122.0 parts (1.0 mol) of benzoic acid and 1.7 parts of methane sulfonic acid (as a catalyst) was stirred and heated under nitrogen to a temperature of 170° C. while collecting any distillate formed. When no more distillate came over and the acidity was less than 3 mg, it was cooled to 50° C. and washed. After washing again with a dilute salt solution, the ester layer was separated and heated under vacuum to remove traces of water. The benzoate ester composition was a clear liquid with a surprisingly low odor.

EXAMPLE 2

A mixture of 207 parts (1.0 mol) of NEODOL 25 alcohol, 122 parts (1.0 mol) of benzoic acid and 1.6 parts of methane sulfonic acid catalyst was heated under nitrogen to 170°–175° C. with stirring. The reaction was held at this temperature for approximately 4 hours, collecting distillate formed until acidity dropped below 5 mg. The product was then cooled to 50° C., neutralized, washed and vacuum stripped to remove any excess residual water. The final benzoate ester composition was an almost colorless liquid with very low odor.

EXAMPLE 3

The previous Example 1 was repeated using 207 g (1.0 mol) of NEODOL 25 alcohol, 128.1 g (1.05 mol) of benzoic acid and 6 g of methane sulfonic acid. The reaction was run until acidity dropped below 10 mg. It was then cooled, neutralized, washed and vacuum stripped to remove any excess residual water. The product was an almost colorless liquid benzoate ester composition with very low odor.

EXAMPLE 4

Example 1 was repeated using 213 g (1.1 mol) of the aforedescribed NEODOL 23 alcohol and heating at 170°–175° C. for 3 hours. The benzoate composition after washing and vacuum stripping was a clear, almost colorless liquid with very low odor.

EXAMPLE 5

A mixture of 240 g. (1.1 mol) of the aforedescribed NEODOL 45, 122 g. (1.0 mol) of benzoic acid and 1.8 g of methane sulfonic acid (as a catalyst) was heated under nitrogen with stirring to 170°–175° C. and held at this temperature for two hours until no more distillate was collected. The yield after washing and vacuum stripping was 660 g. (97%) of a clear liquid benzoate product with very low odor.

EXAMPLE 6

In a manner similar to Example 1, the benzoic acid esters were made of NEODOL 23, NEODOL 45 and a 1:1 weight basis of NEODOL 23 and NEODOL 45.

PROPERTIES OF AND USES FOR BENZOIC ACID ESTER COMPOSITIONS

EXAMPLE 7

GREASINESS

A comparison of the composition of the present invention was undertaken with a single benzoate ester falling within the carbon chain length range encompassed in the mixtures of the invention. In particular, there was utilized in this comparison, a sample of the composition of this invention corresponding to the benzoic acid ester of NEODOL 25 alcohol. This ester product is the benzoic acid ester of a mixture of $C_{12}$, $C_{13}$, $C_{14}$ and $C_{15}$ alcohols corresponding to that contained in the NEODOL 25 alcohol. This product was compared with a myristyl ($C_{14}$) benzoate, which was prepared by a similar procedure to that described in Example 1, i.e., by reaction of myristyl alcohol with benzoic acid under conditions essentially corresponding to those of Example 1.

It was found that the myristyl benzoate is a much heavier product, virtually a solid at ambient room temperature, i.e., 70°–73° F. The application of a drop of myristyl benzoate to the skin was found to be still evident one-half hour after rub-in of same, whereas the ester composition of this invention, although giving the feeling of emolliency, did not display the sheen associated with the presence of a greasy substance as did the myristyl benzoate.

It may be noted that the foregoing result is deemed completely unexpected, since the ester composition of this invention may be thought to include as one component thereof a $C_{14}$ myristyl benzoate; and yet in the mixture defined in the invention the properties are completely dissimilar in the extremely important characteristic just discussed.

EXAMPLE 8

OILINESS

In this Example further evaluation of oiliness was effected for compositions in accordance with the invention. More specifically, four ester compositions were compared: (1) A benzoic acid ester of NEODOL 25 alcohol prepared as in Example 1; (2) An ester composition prepared by the reaction of NEODOL 23 alcohol with benzoic acid, essentially under the conditions of Example 1; (3) An ester composition prepared by the reaction of NEODOL 45 alcohol with benzoic acid, essentially under the conditions of Example 1; (4) An ester composition prepared by mixing on a 1:1 weight basis NEODOL 23 and NEODOL 45 alcohols and reacting that mix with benzoic acid essentially under the conditions of Example 1.

The tests conducted were subjective in nature—10 individuals were requested to evaluate the above mentioned characteristics using a scale of 1 to equal "least" to 4 for "most". The results are set forth in Table I below, from which it will be seen that the NEODOL 25 ester compositions are preferred over other NEODOL ester compositions.

TABLE I

| Product | Oiliness |
| --- | --- |
| NEODOL 25 benzoates | 1 |
| NEODOL 23 benzoates | 3 |
| NEODOL 45 benzoates | 3 |
| NEODOL 23/45 (1:1) benzoates | 2+ |
| Myristyl (C14) benzoate | 4 |

However, all of the NEODOL ester composition are superior to myristyl ($C_{14}$) benzoate.

EXAMPLE 9

CLOUD POINT AND POUR POINT

"Cloud point", refers to the temperature at which a waxy solid material appears as the liquid composition being examined is cooled. Cloud points are also associated with pour points, which is the lowest temperature at which a liquid will flow when a container is inverted. In all cases as the temperature is lowered, the cloud point is detected first, with the pour point being generally 5°–25° F. lower.

It is an important characteristic of formulation development for toiletries and the like to utilize a product that has as low a cloud point as possible. This is a necessary requirement to prevent irreversible changes from occuring during the lifetime of a toiletry product exposed to varying ambient temperatures of, e.g., −15° C. to 48° C.

Whereas myristyl benzoate has a cloud point determined at 21° C., the benzoic acid ester of NEODOL 25 of the present invention, was found to have an astonishingly low cloud point of below 0° C., and a pour point approaching −14° C. This is of enormous importance for storage of large quantities of a particular raw material in unheated warehouses during winter.

The benzoic acid ester of NEODOL 23 exhibited a cloud point of about −4° C. and a pour point of about −6° C.

The benzoic acid ester of NEODOL 45 exhibited a cloud point of about 9° C., and a pour point of about 4° C.

The benzoic acid ester of a 1:1 weight basis mixture of NEODOL 23 and NEODOL 45 exhibited a cloud point of about −4° C., and a pour point of about −9° C.

EXAMPLE 10

ODOR

Referring now to the characteristics of odor: Lack of odor is of enormous important in the development of consumer-oriented products. Many emollients have a characteristic odor that is obnoxious and in many cases difficult to mask. Where masking is possible, it is accomplished only at great expense.

Completely unexpectedly, it has been found that the compositions of the present invention are for all practical purposes lacking in odor. A direct comparison was made, e.g., between the benzoic acid ester of NEODOL 25 and myristyl benzoate—and yielded startling results. Myristyl benzoate has a pungent fatty odor, making it unacceptable, e.g., as a fragrance diluent, whereas the product of the invention is completely bland.

Similar tests were performed with the benzoic acid esters of NEODOL 23, NEODOL 45 and a 1:1 weight basis mixture of NEODOL 23 and NEODOL 45. These esters exhibited a substantially bland odor.

The significance of this lack of odor may be appreciated (e.g., in fragrance applications) by observing that all formulas has a minimum fragrance level (MFL), at which the formula no longer has an inherent odor. However, even at this MFL the notes of the fragrance itself are not noticeable. A slight increase in fragrance level must be effected to be able to detect the fragrance oil, and using the benzoic acid ester of NEODOL 25, a level of 0.25% can be used to overcome the inherent odor of the formula, to establish a detectable level of fragrance. Myristyl benzoate on the contrary, requires a figure much in excess of 0.25%—and here it must be borne in mind that for every 0.1 pound increase, the cost per hundred pounds of finished product (in this hypothetical example) increases eighty cents.

EXAMPLE 11

ODOR

In this Example, a further evaluation of odor was effected for compositions in accordance with the invention. More specifically, the aforedescribed four products set forth in the previous Examples, were compared by again requesting ten individuals to evaluate odor using a scale of 1 to equal "least" to 4 "most". The results are set forth in Table II below, from which it will be again seen that the benzoic acid esters of NEODOL 25 are preferred.

TABLE II

| Product | Odor |
| --- | --- |
| NEODOL 25 benzoates | 1 |
| NEODOL 23 benzoates | Above 2 |
| NEODOL 45 benzoates | 3 |
| NEODOL 23/45 (1:1) benzoates | Above 1 |

Myristyl benzoate's pungent fatty odor was vastly inferior to the odor of any of the foregoing benzoic acid esters.

EXAMPLE 12

GEL FORMATION/SETTLING

Gel formation refers to the ability of an emollient oil to form gels with suspending agents such as quaternized hectorite (such as Bentone 38) or stearalkonium (Bentone 37). This is a desirable characteristic as it provides the formulator a means of suspending many actives such as aluminum chlorhydrate and pigments in anhydrous systems. The former is particularly useful in aerosol and stick-type antiperspirants; the latter in such products as lipsticks, stick rouge, and other facial makeup products.

Such gels should exhibit absence of syneresis, i.e., the contraction of a gel on standing with the subsequent exudation of liquid; high viscosity; temperature stability; and ability to suspend matter. The presence of syneresis negates the bulk storage of a Bentone Gel (10% stearalkonium hectorite or quaternium-18 hectorite suspension in an anhydrous solvent), as it requires equipment and expertise not normally available in many manufacturing facilities to enable the gel to be reconstituted to a homogeneous condition prior to use.

The viscosity of a gel is dependent on the polarity of the organic liquid it is suspended in. The more polar the liquid, the lower the viscosity. Non-polar or low polarity organic liquids result in higher viscosities. Completely non-polar liquids may present a problem in that too high viscosities results in a low percentage of a gellant. Upon further dilution (as normally occurs in formulation work), the ability to suspend matter can be lost in these instances.

In tests, it was found that when a semi-solid such as the aforementioned myristyl benzoate, is used as the organic liquid, a requirement is created for an abnormal amount of mechanical, chemical, and thermal energy; and this results in a gel with abnormally high viscosities.

Desirably, basic gel cocentrates and formulation containing same, should show stability to a wide range of temperatures without phase separation—which would destroy the gel viscosity and suspending capabilities. In addition, the basic function of such gels is to suspend an active material present in a formulation as a particulate matter. In a system such as aerosol antiperspirants, the active is aluminum chlorhydrate present as insoluble particulates, with a particle size ranging from submicron to about 50 microns. Before use, the container is shaken to re-dispense the particulates in suspension as to provide the proper dosage of activities. Re-dispersion should be immediate, complete, and last for a period of time sufficient for proper application. Longer times are indeed more beneficial as it provides a lower misuse factor.

With most solvents, including specifically the aforementioned myristyl benzoate, it was found that settling occurs within 60 to 90 seconds. Completely unexpectedly, it was, however, found that when the products of the present invention, specifically including the benzoic acid ester of NEODOL 25, were so used, settling times increased to 4 to 7 minutes. Further, the products when settled, did not hard-pack—so that they were easily redispersed. This property of the however, found that when the products of the present invention, specifically including the benzoic acid ester of NEODOL 25, were so used, settling times increased to 4 to 7 minutes. Further, the products when settled, did not hard-pack—so that they were easily redispersed. This property of the esters of the present invention is completely unexpected; and is of enormous utility for typical applications of the said esters.

EXAMPLE 13

TOXICITY

Products of the type in which the present esters are incorporated, invariably come in contact with the consumer. In other instances, such as represented by Example 45 which is pertinent to textile manufacturing, the products of the type in which the present esters are incorporated will come in contact with the workers. Great care and caution are therefore exercised by manufacturers, and by state and federal agencies to insure the use of raw materials that are innocuous and free from harmful contaminants. Toxicity studies pertinent to the present compositions were accordingly conducted. It was unexpectedly found that for the benzoic acid ester of NEODOL 25, the results on acute oral toxicity (rate), $LD_{50}$, was 34.5 g/kg of body weight. Industry normally considers a product having an $LD_{50}$ of greater than 5 g/kg as adequate. These results establish extremely low toxicity. While precisely comparative data for myristyl benzoate is not available, the significance of the present finding may be appreciated by noting that the very commonly used ester, butyl benzoate has an $LD_{50}$ of 3.5 g/kg of body weight. Thus the product of the invention has a toxicity only 1/10th that of a chemically somewhat analogous product—which is extremely unexpected.

EXAMPLE 14

EASE OF EMULSIFICATION

In this Example, the emulsifying properties of the compositions of the invention were compared to various commonly used solvents and to mixes of benzoates.

Tests were conducted by adding exactly 20 ml of toluene to 20 ml of the test solvent in a glass stoppered cylinder and shaking to mix. When mixed, 20 ml of water was then added, the resulting mixture warmed to 40° C. and shaken 30 times. This was allowed to stand for 15 minutes and the upper layer analyzed for water content by the Karl Fisher titration method. Results are set forth in the following Table III:

TABLE III

| Test Solvent | % Water in Oil Phase (upper layer; by K-F Method) |
|---|---|
| NEODOL 25 benzoates | 0.69 |
| IPM (isopropyl myristate) | 0.12 |
| IPP (isopropyl palmitate) | 0.66 |
| Mineral Oil | less than 0.10 |
| Octyl Isononanoate | 0.26 |
| NEODOL 23 benzoates | 0.28 |
| NEODOL 25 benzoates | 0.28 |
| NEODOL 23/45 (1:1) benzoates | 0.36 |

These results show that the preferred NEODOL 25 benzoate has greater emulsifying properties than the other commonly used solvents, and is better than the NEODOL 23 or NEODOL 25 benzoates. The benzoic acid ester of the blend of NEODOL 23 and NEODOL 45, provides less emulsification than the benzoic acid ester of NEODOL 25—the latter being preferred.

EXAMPLE 15

ODOR, TOXICITY AND FEEL PROPERTIES

COMPARISON OF ALCOHOL AND ITS BENZOATE ESTER

For typical applications to which the ester products of this invention are used, there are three characteristics which are of utmost importance. These are:

(1) odor;

(2) toxicity and safety, and irritation to the eyes and skin; and (3) feel when applied to skin.

As regards the first factor, namely odor: Lack of odor is of enormous importance in consumer oriented products such as toiletries and cosmetics. The NEODOL 25 alcohol is found when evaluated from this viewpoint to have a typical "fatty" odor, subjectively suggesting an "oiliness". Different individuals will respond differently to such odor, but the odor is quite marked. In comparison, the benzoic acid ester of NEODOL 25 is found to be virtually lacking in detectable odor.

As for the second characteristic, i.e., toxicity, it is emphasized that products of the type in which the present esters are used, invariably come in contact with the consumer. Great care and caution are therefore exercised by manufacturers and state and federal agencies to ensure the use of raw materials that are innocuous and free from harmful contaminants. In the following Table, the ester compositions of the present invention are compared with the NEODOL 25 alcohol with respect to toxicological studies. The compositions of this invention are seen to be non-irritating to the eyes and non-irritating and non-sensitizing to the human skin. Acute oral toxicity is extremely high, showing the products of the invention to be remarkably safe if accidently ingested.

TOXICOLOGY

| Characteristic Test | NEODOL 25 | NEODOL 25 Benzoates of This Invention |
|---|---|---|
| Acute Oral Toxicity (Rats), $LD_{50}$ | 23.1g/kg | 34.5g/kg |
| Ocular Irritation (Rabbits), No Wash | Minimal | 0.0 |
| Acute Dermal Irritation (Rabbits), $LD_{50}$ | 6.18g/kg[(a)] | 2.0g/kg, Non-toxic |

-continued

| Characteristic Test | TOXICOLOGY | |
|---|---|---|
| | NEODOL 25 | NEODOL 25 Benzoates of This Invention |
| Primary Dermal Irritation Index (Rabbits) | Mild | 0.008 |
| Acute Inhalation Toxicity (Rats), $LD_{50}$ | No Data From Supplier | 2.0 mg/kg. Non-toxic |
| Guinea Pig Sensitization' | No Data From Supplier | Not a Potential Sensitizer |
| Comedogenicity Assay (Rabbits) | No Data From Supplier | Non-comedogenic |
| Repeated Insult Patch Test (Humans) | Very Slight Irritation[b] Non-fatiguing or Sensitizing | Non-irritating and Non-sensitizing to all human subjects tested[c] |

[a] 50% NEODOL 25 w/v in the monomethylether of dipropylene glycol
[b] 1% NEODOL w/v in alcohol
[c] 10% Benzoates of Invention w/v/ in mineral oil NOTES:
1. All toxicological studies of NEODOL 25 and of Benzoates of Invention are based on 100% active except as noted in Table (a), (b), and (c).
2. Toxicological data reported on NEODOL 25 obtained from page 23 of NEODOL Booklet SC:7-798 printed in USA 7/79 SM.

"Greasiness" is a term applied to a product or formula containing such product, that is suggestive of or resembles something greased; i.e., it has a slick, unctuous character which manifests its presence easily, even to the laymen. Applied to skin, for example, it thus produces a distinct glossiness, which although not considered too detrimental in itself, also results in a slick, greased hand, resulting in a messy, unsightly condition which offends consumers. When the NEODOL 25 alcohol is applied to the skin, it produces a moderately dry feel. By contrast, when the benzoate ester product of the NEODOL 25 is applied to the skin, a drier, talc-like feeling is produced, one which is completely lacking in any suggestion of oiliness or greasiness. The feeling is regarded by individuals who are requested to comment upon same, as being a pleasant sensation—as mentioned, the comparison is usually stated that the feeling is analogous to applications of talc. When both the NEODOL 25 alcohol and its benzoate ester are each blended with an equal amount of mineral oil, a well-known oily feeling material, the blend of the benzoate ester composition and mineral oil produces a dry feel to the skin, eliminating the oily feel of the mineral oil. The blend of NEODOL 25 alcohol and mineral oil does lower the oily feel of mineral oil, but not completely.

Thus, the products of the present invention, in all important characteristics for the uses of same in toiletries, cosmetics and the like, are completely distinctive from and superior to the NEODOL 25 alcohol composition.

EXAMPLE 16

STABILITY

A most unusual and unexpected property of the benzoate esters of this invention is the remarkable chemical stability to hydrolysis over a pH range of approximately 2 to 12. To applicant's knowledge, all currently used ester compositions, i.e., compositions used in the type of applications for which the instant products find application, hydrolyze within this pH range, i.e., these prior art esters within at least a portion of the indicated pH range, will decompose by hydrolysis.

EXAMPLE 17

TOILETRY AND COSMETIC FORMULATIONS CONTAINING BENZOIC ACID ESTERS

To further demonstrate the uniqueness of the compositions of this invention, a series of simple formulas were prepared comparing the appearance, pH and viscosities of various toiletry and cosmetic products formulated with the compositions of the invention, and with other esters and the like which commonly function in similar capacities in the products considered. The products specifically considered included:

(1) a hair cream;
(2) a hand cleaner;
(3) dispersible bath oil;
(4) a suntan oil;
(5) a floating bath oil; and
(6) a brilliantine.

These are deemed to be highly representative of formulations wherein the products of the invention find widespread application. The results are set forth in the Table following:

TABLE V

| | HAIR CREAM | | HAND CLEANER | |
|---|---|---|---|---|
| Component | A Parts | B Parts | C Parts | D Parts |
| Pluronic F-127* | 5.0 | 5.0 | — | — |
| Pluronic L-92* | 2.5 | 2.5 | — | — |
| Veegum** | 1.0 | 2.0 | — | — |
| Cetyl Alcohol | — | — | 2.0 | 2.0 |
| NEODOL 25 benzoates | — | 25.0 | — | 25.0 |
| NEODOL 23 benzoates | 25.0 | — | 25.0 | — |
| Solulan 75+ | — | — | 3.0 | 3.0 |
| Solulan 98+ | 5.0 | 5.0 | — | — |
| Glyceryl monostearate | 2.0 | 2.0 | 5.0 | 5.0 |
| Stearic Acid | — | — | 5.0 | 5.0 |
| Myristyl Alcohol | — | — | — | — |
| Vancide 89 RE++ | 0.5 | 0.5 | — | — |
| Citric Acid | 0.1 | 0.1 | — | — |
| Glycerin | — | — | 5.0 | 5.0 |
| Triethanolamine | — | — | 2.0 | 2.0 |
| Water | 58.7 | 58.7 | 53.0 | 53.0 |
| Appearance | White Liquid | White Liquid | Stif off-white paste | as A, but creamier |
| pH | 5.0 | 5.5 | 8.2 | 8.7 |
| Viscosity, cps | 130 | 912 | 27,600 | 37,200 |

*Block polymer surfactant (BASF Wyandote)
**magnesium aluminium silicate (RT Vanderbilt)
+ a lanolin-based auxiliary emulsifier (Americhol Corp.)
++ mercaptain fungicide (RT Vanderbilt)

Evaluation:
Formula A is thin, difficult to apply
Formula B is suitable
Formula C is granular in appearance
Formula D is an appealing stiff cream

TABLE VI

|  | DisPERSIBLE BATH OIL | | SUN TAN OIL | | FLOATING BATH OIL | | BRILLIANTINE | |
|---|---|---|---|---|---|---|---|---|
|  | E Parts | F Parts | G Parts | H Parts | I Parts | J Parts | K Parts | L Parts |
| Modulan* | 5.0 | 5.0 | — | — | — | — | — | — |
| Acetulan** | 5.0 | 5.0 | — | — | — | — | 5.0 | 5.0 |
| NEODOL 23 benzoates | 60.0 | — | 85.8 | — | 95.0 | — | 95.0 | — |
| NEODOL 25 benzoates | — | 60.0 | — | 85.8 | — | 95.0 | — | 95.0 |
| Ethyl Alcohol | — | — | 10.0 | 10.0 | — | — | — | — |
| Escalol 507+ | — | — | 1.2 | 1.2 | — | — | — | — |
| Mineral Oil | 24.5 | 24.5 | — | — | — | — | — | — |
| Lanoil*** | — | — | 2.5 | 2.5 | — | — | — | — |
| PEG 400 Dilaurate++ | 5.0 | 5.0 | — | — | — | — | — | — |
| Pluronic L-92 | — | — | — | — | 1.0 | 1.0 | — | — |
| Appearance | Hazy Yellow | Clear Yellow | Hazy Tan | Cloudy Straw | Cloudy | Clear | Hazy | Clear |
| pH | 5.5 | 6.0 | 5.7 | 6.2 | 5.7 | 6.3 | 5.6 | 6.2 |
| Viscosity cps | 42 | 43 | — | — | — | — | — | — |

*Modified lanolin (Amerchol Corp.) **Lanolin based derivative (Amerchol Corp.)
+Amino isooctyl PBA (Van Dyk & Co.)
***Lanolin oil (Lanotex)
++Polyethylene glycol (Diamond Shamrock Corp.)
Evaluation:
Formulas E, G, I, and K are less suitable due to their hazy appearance and very slight odor.
Formulas F, H, J and L are more suitable, due to their crystal clarity and lack of odor
*Again, the NEODOL 25 benzoates are preferred over the NEODOL 23 benzoates, however, it is believed that with slight adjustments to the NEODOL 23 benzoates, improved formulations can be made.

EXAMPLE 18

ANTIPERSPIRANT COMPOSITIONS

The use of the compositions of this invention and their unexpected properties is further illustrated by the following Examples, wherein comparative Examples A and B are prior art compositions, and comparative Example C is a control formulation.

COMPARATIVE EXAMPLE A

In this Example a prior art aerosol antiperspirant composition was prepared, which utilized isopropyl myristate as a carrier. The formulation of the composition was as follows:

| Component | % by Weight |
|---|---|
| Bentone 38* | 0.7 |
| Ethanol** | 0.7 |
| Isopropyl myristate | 16.2 |
| Aluminium cholorhydrate+ | 5.9 |
| Propellant++ | 76.5 |

*Trademark of National Lead Co., for organic derivitives of hydrous magnesium aluminium silicate minerals, utilized here as a particulate suspending agent
**SDA-40 grade, 95%
+ Composition utilized was "Micro-Dry" product of Reheis Chemical Co., which is a 5/6 basics formulation
++"Propellant A-46" of Phillips Petroleum Co., which is a blend of isobutane, butane and propane This conventional composition when sprayed upon the skin left a relatively oily feeling residue. When the composition was agitated, it took approximately 150 seconds for settling of the suspended matter.

COMPARATIVE EXAMPLE B

In this Example, another prior art aerosol composition was prepared, utilizing a volatile silicone as a carrier, i.e., in place of isopropyl myristate. The formulation of the composition were as follows, where the components other than the volatile silicone are as identified in Example A.

| Component | % by Weight |
|---|---|
| Bentone 38 | 0.7 |
| Ethanol | 0.7 |
| Volatile silicone* | 16.2 |
| Aluminum chlorohydrate | 5.9 |
| Propellant | 76.5 |

*Composition utilized was SWS 03314, a volatile cyclic silicone oil which is a product of SWS Silicones Corp. of Adrian, Michigan, and which may be represented by the formula:

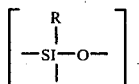

where R is 1 to 3 carbon alkyl group and preferably a methyl group, and n is a number from 3 to about 10 and preferably 3 to 7, which are then joined together to form a cyclic structure.

The volatile silicone provides certain advantages to the composition of this Example—vis-a-vis the composition of Comparative Example A. The present composition when sprayed upon the skin, e.g., leaves a less oily-feeling residue. Moreover, onset of efficacy is more rapid with this composition because the silicone is less hydrophobic than is the IPM. On the other hand, it was found that following agitation of this composition, it took approximately 50 seconds for settling of the suspended matter. Such rapid settling is quite undesirable since uniformity of the suspension is desired for a relatively long period in order to maintain uniformity during use, from use to use, and to avoid clogging of the aerosol valve, etc.

COMPARATIVE EXAMPLE C

For purposes of providing control data for comparing the unexpected properties of the compositions of this invention, another aerosol antiperspirant composition was prepared, wherein a combination of isopropyl myristate and a volatile silicone was used as a carrier. The formulation of this composition was as follows, where all components are as identified in Comparative Examples A and B:

| Component | % by Weight |
| --- | --- |
| Bentone 38 | 0.7 |
| Ethanol | 0.7 |
| Isopropyl myristate | 8.0 |
| Volatile silicone | 8.2 |
| Aluminum chlorhydrate | 5.9 |
| Propellant | 76.5 |

The above composition was found to require approximately 100 seconds for settling following agitation.

EXAMPLE D

In this Example, an aerosol antiperspirant composition containing the composition of this invention was prepared, wherein the carrier was the benzoic acid ester of NEODOL 25. The formulation of this composition was as follows, where all components, are as identified in Comparative Examples A through C.

| Component | % by Weight |
| --- | --- |
| Bentone 38 | 0.7 |
| Ethanol | 0.7 |
| NEODOL 25 benzoates | 16.2 |
| Aluminum chlorhydrate | 5.9 |
| Propellant | 76.5 |

The composition of this Example when sprayed upon the skin, left a residue that was neither oily nor greasy to the touch; and such residue was odor-free. Onset of efficacy was more rapid with this composition than with that of Comparative Examples A and C. Following agitation of the composition, approximately 160 seconds were required for settling of the suspended matter. In addition, the packing of the settled matter was "soft", which is a desirable characteristic in that subsequent agitation is then able to readily re-suspend the particulate matter.

EXAMPLE E

In this Example, another aerosol antiperspirant composition was prepared using the benzoic acid ester of NEODOL 25 mixed with a volatile silicone of the type described in Comparative Examples B and C. The formulation of this composition was as follows; where all components are as identified in Comparative Examples A and B:

| Component | % by Weight |
| --- | --- |
| Bentone 28 | 0.7 |
| Ethanol | 0.7 |
| NEODOL 25 benzoate | 8.0 |
| Volatile silicone | 8.2 |
| Aluminum chlorhydrate | 5.9 |
| Propellant | 76.5 |

The composition of this Example, when sprayed upon the skin, exhibited all of the positive properties of the previous composition, using the benzoate esters as the sole carrier. It was unexpectedly found, however, that the present composition, following agitation, took approximately 250 seconds for settling of the suspended matter. Comparison with Comparative Example B, and the previous Example D, will render clear the synergistic action that has occurred. Thus, in Comparative Example B, where the volatile silicone is used alone, the settling time was 50 seconds; and where in Example D the benzoate esters are used as the sole carriers, settling time was 150 seconds.

EXAMPLE 19

PERFUME AND COLOGNES

Perfumes, colognes, or the like prepared using the compositions of the present invention have outstanding attributes in that the benzoate esters of this invention, when utilized as a vehicle, impart practically no odor of their own to the perfume or cologne. In addition, the perfume or cologne compositions when applied to the skin, produce a pleasant sensation, and induce conditioning of the skin. A representative perfume formulation was prepared, utilizing the following components in the indicated proportions:

| Component | & by Weight |
| --- | --- |
| Compounded fragrance oil | 10. |
| NEODOL 25 benzoate | 10. |
| S.D. (speciallydenatured) alcohol, anhydrous | approx. 79–80 |
| Color | |
| Antioxidant | q.s |

In preparing the perfume of this Example, the alcohol was combined with the antioxidant and mixed to dissolve. Thereupon the benzoate esters and fragrance oil were added and mixed. The resulting composition was chilled to 0° C., mixed, a filter aid added, and filtering carried out. As required, color was added, mixed, and the final perfume composition was then ready for packaging. The resultant perfume composition was found to be a clear solution with the fragrance exhibiting its true character. The fixative nature of the vehicle was found to allow the fragrance to be sensed for a very extended period.

EXAMPLE 20

BATH PRODUCTS

There are many types of bath products. The major ones are:
1. Bath salts
2. Floating bath oils
3. Dispersible bath oils
4. Emulsifiable bath oils
5. Soluble bath oils
6. Bath gels
7. Foaming bath oils
8. Aerosol bath oils
9. Specialty baths
10. Bubble baths All but bath salts and specialty baths contain oils as the major component. Many bath products contain oils as an additive.

Because of the drying effect to the skin from soaking in a bath utilizing a soap or synthetic detergent for cleansing purposes, the consumer wants to overcome this dryness. This dryness is due to oil removal from the skin by the detergent. Bath oils and emollient oils in detergent bath products impart emolliency and eliminate dryness to the skin. What is generally undesirable is the use of an emollient oil which is very oily or greasy as is the case with mineral oil.

There are 2 major problems with using an oil which imparts an oily feel to the skin; namely, the body feels excessively oily and slipping in the tub can lead to injury. Also, a bath tub ring is formed.

Oils properly formulated are deposited on the skin by the bath. The benzoic acid esters in a bath oil product are deposited on the skin and leave a non-oily dry lubricating, velvety feel on the skin. Even in the presence of mineral oil, the ester will impart this same non-oily dry lubricating velvety feel to the skin. Should a light oily feel be desired, a large excess of mineral oil and a significant lower concentration of ester will produce this slight oily effect.

In addition to a dry lubricating feel to the skin, one other important property which the oil should possess is being toxicologically non-irritating and non-sensitizing. The benzoate esters are non-irritating and non-sensitizing to the skin. This conclusion is reached from tests on rabbits, guinea pigs, and humans. These properties, i.e. dry feel, non-irritation and non-sensitizing are unexpected. Isopropyl myristate, commonly used in bath products, has been suspect as an irritant.

BATH OIL

An example of a simple floating bath oil is as follows:

| FLOATING BATH OIL | |
|---|---|
| Benzoate ester of NEODOL 25 | 95% |
| Plurnonic L-92 (with ethoxylated (20%)/propoxylated (80%) nonionic) - (BASF-Wyandotte) | 1% |
| Fragrance | 4% |

Because of the high Spreading Coefficient of the ester of 34.5 dynes/cm, this oil or cosmetic fluid spreads well. Isopropyl myristate (IPM) has a Spreading Coefficient of 17.7 dynes/cm, one-half of that of the ester. The higher the Spreading Coefficient, the greater the spreadability. Also interfacial tension against water at 25° C. of the ester is 7.14 dynes/cm whereas that of IPM is appreciably higher at 17. dynes/cm. This low interfacial tension against water and high Spreading Coefficient of the esters are unexpected. The above floating bath oil leaves a dry lubricating velvety feel to the skin.

An example of a simple dispersible bath oil is:

| DISPERSIBLE BATH OIL | |
|---|---|
| Benzoate ester of NEODOL 25 | 97% |
| Oleth - 10* | 3% |

*Ethoxylated (10%) oleyl alcohol.

Again, a dry lubricating feel is imparted to the skin. Another example of a dispersible bath oil is:

| DISPERSIBLE BATH OIL | % By Wt. |
|---|---|
| Benzoate ester of NEODOL 25 | 60.0 |
| Mineral Oil | 24.5 |
| Modulan[1] | 5.0 |
| Acetulan[1] | 5.0 |
| PEG-400 Dilaurate | 5.0 |
| Fragrance, F1126 | 0.5 |

[1]Amerchol, a unit of CPC Int'l, Edison, N.J. 08902.

PROCEDURE

Materials added in order listed and stirred.

ADVANTAGE

The benzoate ester reduces oiliness of mineral oil.

Here a significantly large amount of mineral oil is used with the ester in a ratio of 3.25:1. Surprisingly, a dry lubricating feel is imparted to the skin.

Another example of a dispersible bath oil is:

| | "STAY CLEAR" BATH OIL No Greasy Film. No Lanolin Drop Out. | |
|---|---|---|
| | | % by wt. |
| (A) | Light mineral oil, N.F. | 45.00 |
| | Benzoate ester/NEODOL 25 | 25.00 |
| | Lanolin oil | 2.50 |
| | Fragrances (s) | 0.60 |
| | PEG 400 dilaurate | 0.60 |
| | PEG 200 DILAURATE | 3.60 |
| (B) | **Benzoate ester NEODOL 25 | 2.00 |
| | D & C Violet #2 | 0.0002 |
| | Antioxidant G-16[1] | 0.05 |
| (C) | PEG 200 DILAURATE | 0.08 |
| | Uvinul M-40[2] | 0.005 |
| (D) | Light mineral oil, N.F. | 19.85 |

**If desired, prepare a stock solution and store in the dark for a later use.
[1]Griffith Laboratories, Inc., Jersey City, N.J. 07303
[2]GAF Corp., N.Y., N.Y. 10020

PROCEDURE

1. Combine and mix (A) in order listed.
2. Combine and mix (B) for 5 minutes and add to (A) with mixing.
3. Combine, mix and dissolve (C) and add to above and mix for 5 minutes.
4. Add (D) and mix total batch for about 25 minutes.

In this formulation, there is about 65% mineral oil plus 2.5% lanolin oil along with 25% ester. This is a quick blooming bath oil and there is no lanolin drop out. A dry lubricating velvety feel is imparted to the skin.

Many bubble bath or foaming bath oils do not contain an oil but are based on alkanolamide detergents.

An example of a Bubble Bath Oil (or foaming bath oil) is shown below:

| | BUBBLE BATH OIL | % by wt. |
|---|---|---|
| (A) | TEA-Lauryl Sulfate, 40% | 40.0 |
| | Disodium Monoricinoleamide MEA-Sulfosuccinate[2] | 1.5 |
| | Linoleamide DEA[1] | 7.0 |
| | Laneth-16 | 5.0 |
| | Benzoate ester of NEODOL 25 | 3.0 |
| | PEG-7 Glycerol Cocoate[3] | 1.0 |
| | Polysorbate 20 | 3.0 |
| | Tetasodium EDTA | 0.1 |
| (B) | Water, purified | 36.5 |
| (C) | Water, purified | 2.0 |
| | Quanternium-15[4] | 0.2 |
| (D) | Fragrance | 0.7 |
| (E) | Color | q.s. |

[1]Aminol LNO (FINETEX)
[2]Rewoderm S-1333 (Rewo, Div. Emery Ind.)
[3]Standamul HE (Henkel)
[4]Dowicil 200 (Dow Chemical Co.)

PROCEDURE

1. Combine and mix (A). Heat and mix to 75° C.
2. Heat (B) to 76°-78° C. Add to (A).
3. Mix and cool to 41°-43° C.
4. Mix (C) and add to above mix.
5. Add (D) and (E); mix and cool to 20°-24° C.

ADVANTAGE

A true bubble bath oil with long lasting bubbles and a luxurious after feel.

A problem of bubble bath is the defatting of skin by the detergents. As little as 3% ester provided a dry emollient after-feel while not significantly altering the foaming properties of the detergents. Esters are known to appreciably affect the foaming properties of detergents and are considered foam suppressants. This was another unexpected property of the esters.

BATH GELEE SACHET (JR#2-35-01)

An example of a soap bar or soap/syndet bar or syndet bar containing an emollient oil.

Toilet soap bars were prepared in commercial soap equipment containing essentially:

| Soap | 97.5% |
|---|---|
| Benzoate ester NEODOL 25 | 2.0% |
| Fragrance | 0.5% |
| Color | q.s. |

Surprisingly in a blind study the user readily observed a richer and denser lather compared to what he or she was used to from a regular soap. Upon rinsing and drying, a slight dry emollient feel was discovered. Larger concentrations of esters improve the degree of dry emolliency. The imparted emolliency is desired by the consumer since soap is defatting to the skin.

BATH OIL

In this Example, a satinized, protein bath oil was prepared using the benzoate ester as the emollient carrier. More specifically, four sub-mixtures A, B, C, D, were initially prepared which included individual components as follows:

|   | Component | % by Weight |
|---|---|---|
| A. | light mineral oil, N.F.** | 42.00 |
|   | benzoate esters* | 23.00 |
|   | lanolin oil** | 2.50 |
|   | fragrances | 0.60 |
|   | PEG-8 dilaurate** | 0.60 |
|   | Lexein A440[1] | 5.00 |
|   | PEG-4 dilaurate | 3.60 |
| B. | benzoate esters* | 2.00 |
|   | D & C Violet #2** | 0.0002 |
|   | D & C Green #6** | 0.0001 |
|   | antioxidant | 0.05 |
| C. | PEG-4 dilaurate** | 0.80 |
|   | benzophenone-4** | 0.005 |
| D. | light mineral oil | 19.85 |

[1]Myristyl hydrolyzed animal protein product of Inolex Corp., Chicago, Illinois 60609
*The benzoate esters utilized in this Example were the benzoic acid esters of NEODOL 25.
**Identification is in accordance with the CTFA Cosmetic Ingredient Dictionary, 2nd Ed., 1977. (Published by The Cosmetic Toiletry, and Fragrance Association, Inc., 1135 15th St., NW, Washington, D.C. 20005). Unless otherwise indicated, all name designations in the Examples of this specification shall have the same CTFA reference.

The procedure used in preparing the bath oil of this Example involved an initial combination of the components of submixture A in the order listed therein. The combined components of sub-mixture B were mixed for five minutes and then added to sub-mixture A with additional mixing. The compounds of sub-mixture C were combined, mixed and dissolved, and then added to A and B, with further mixing for five minutes. Finally, the light mineral oil, i.e., sub-mixture D was added; and the total batch mixed for about 25 minutes. The resultant product is essentially an anhydrous solution in which the benzoate esters are a vehicle with the mineral oil. When applied to the skin, it was found to provide a very satiny feel. The moisture-laden protein is effectively locked to the skin by use of the said composition, to produce a soft, comfortable feeling at the skin surface. The product was found to yield a "dry hand", i.e., while acting as a excellent emollient, it nonetheless produced a smooth, nonoily feel upon the skin surface. This was especially suprising in view of the very high quantities of mineral and other oils present in the composition.

EXAMPLE 21

SUNTAN OIL

In this Example, a "suntan oil" was prepared using the ester compositions of this invention. The following components were combined and mixed in the order listed:

| Component | % by Weight |
|---|---|
| Benzoate esters* as vehicle | 85.8 |
| S.D. alcohol | 10.0 |
| Octyl dimethyl PABA | 1.2 |
| Lanolin oil | 2.5 |
| Fragrance | 0.5 |

*Benzoic acid ester of NEODOL 25

The resultant composition was a non-greasy feeling, nontacky oil with excellent spreading characteristics.

EXAMPLE 22

PROTEINIZED SUNTAN OIL

In this Example, a "proteinized suntan oil" was prepared using the compositions of this invention. The components of the composition were as follows:

| Component | % by Weight |
|---|---|
| S.D. alcohol | 70.00 |
| Benzoate esters* as vehicle | 20.00 |
| PEG-8 | 0.25 |
| Hydroxypropyl cellulose | 0.75 |
| Mink amido propyl dimethyl 2-hydroxyethyl ammonium chloride | 0.60 |
| Hydrolyzed animal protein | 5.00 |
| Octyl dimethyl PABA | 3.25 |
| Fragrance | 0.15 |

*benzoic acid ester of NEODOL 25
NEODOL 23 and NEODOL 45 in 1:1 weight ration can be substituted for the benzoic acid ester of NEODOL 25

The alcohol was combined with the PEG-8 and mixed rapidly with addition of the hydroxyethyl cellulose. The resultant product was mixed for 45 minutes and the benzoate esters were then added. The remainder of the components were then added in the order listed, and further mixing was employed. The resultant final product was found to be water-resistant and tack-free on application. Although having a non-greasy feel, it yet displayed excellent emollient properties and prevented drying of the skin.

EXAMPLE 23

SUNSCREEN BUTTER

In this Example, a "sunscreen butter" was prepared using the compositions of this invention. The following components were combined and mixed in the formulation:

| Component | % by Weight |
|---|---|
| NEODOL 25 benzoate | 64.0 |
| NEODOL 25 alcohol | 18.5 |
| Glyceryl C$_{18-36}$ was acid ester | 8.0 |
| Lanolin oil | 6.0 |
| Lanolin alcohol | 1.0 |
| Ethyl dihydroxypropyl PAA | 1.5 |
| Steartrimonium hydrolyzed animal protein | 0.5 |
| Fragrance | 0.5 |

The resultant composition was, again, a non-greasy feeling, dry, lubriating cream composition with excellent spreading characteristics.

EXAMPLE 24

COLD CREAM CLEANSER

In this Example, a cold cream cleanser was prepared using the compositions of this invention. The components of the composition were as follows:

| | Component | % by Weight |
|---|---|---|
| A. | water | 53.60 |
| | propylene glycol | 4.00 |
| | magnesium aluminum stearate | 1.50 |
| B. | glyceryl stearate, S.E. | 7.50 |
| | mineral oil, light, N.F. | 14.80 |
| | benzoate esters* as vehicle | 9.00 |
| | lanolin oil | 0.50 |
| | mineral oil (and) lanolin alcohol | 2.50 |
| | cocyl sarcosine | 0.50 |
| | methyl paraben | 0.10 |
| | antioxidant | 0.50 |
| C. | water | 1.00 |
| | quanternium-15 | 0.10 |
| D. | fragrance | 0.50 |

*Benzoic acid ester of NEODOL 25

In preparing the composition, the components of group A were mixed rapidly for 25 minutes tha then heated to 70° C. The components of group B were then mixed and heated to 70° C. Group B was then added to group A while stirring. With continued stirring, the mix was cooled to 40° C. The components of group C were mixed and added; further stirring was used, and the fragrance (D) was added. The composition was cooled to 25° C. to yield the final product.

The resultant product was an easily spreadable, effective cleansing cream. When applied to the skin, it left same soft and moisturized. Particularly to be noted was that the said product imparted a dry, non-oily lubricating feel—even (as here) in the presence of substantial quantities of mineral oil.

EXAMPLE 25

ELECTRIC PRESHAVE

In this Example, a so-called "electric preshave" lotion was prepared using the ester compositions of this invention. The composition included components as follows:

| | Component | % by Weight |
|---|---|---|
| 1. | S.D. alcohol | 85.8 |
| 2. | Cyclomethicone** | 10.0 |
| 3. | Benzoate esters* | 4.0 |
| 4. | Phenyl dimethicone | 0.1 |
| 5. | Fragrance | 0.1 |
| 6. | Color | q.s. |

*Benzoic acid ester of NEODOL 25
**CTFA designation for volatile silicone

In preparing the composition, components 2, 3, 4, and 5, were mixed and blended; component 6 is added, followed by thorough mixing; thereupon component 1 is added and further thorough mixing applied. The resulting product was a clear fluid which was easily and quickly applied to the face prior to shaving. It dried excess facial moisture and provided excellent lubrication to the face and electric shaver, to aid in providing a close, painless shave. Especially noteworthy was the dry, lubricated feel provided by the composition when applied to the skin. This is sharply contrasted with the oily feel which is present when a generally similar composition is used, which employs conventional IPM as a vehicle.

EXAMPLE 26

EYE AND THROAT OIL

In this Example, an eye and throat oil was prepared in accordance with the invention. The composition included components as follows:

| | Component | % by Weight |
|---|---|---|
| 1. | benzoate esters* | 46.30 |
| 2. | lanolin oil | 7.70 |
| 3. | isopropyl lanolate & lanolin oil | 1.00 |
| 4. | mineral oil, light, N.F. | 44.80 |
| 5. | BHA | 0.05 |
| 6. | propyl paraben | 0.05 |
| 7. | fragrance | 0.10 |

*Benzoic acid ester of NEODOL 25

In preparing the composition, components 1 through 5 were combined and mixed. Component 6 was added and the blend mixed to dissolve. As necessary, the blend was warmed to 48°–50° C. Component 7 was added and the composition mixed for 15 minutes. The final resultant product was a quickly absorbed oil that left the skin with a velvet smooth film. The product had a dry, lubricating feel, even in the presence of very high amounts of mineral and other oils.

EXAMPLE 27

SKIN GEL

In this Example, a "skin gel" was prepared using the ester compositions of this invention. The composition included components as follows:

| Component | % by Weight |
|---|---|
| Glyceryl tribehenate soap | 7.5 |
| Benzoate esters* | 90.5 |
| Fragrance, color, preservative | q.s. |

*Benzoate acid ester of NEODOL 25

In preparing the composition, the first two components were combined, mixed and heated to 110°–115° C. Mixing was continued and the blend cooled to 40°–45° C. The fragrance was added and mixed, and the blend cooled to 25°–27° C. to yield the final product. Such product was found to be a smooth, emollient, greaselessfeeling skin gel, which as quickly absorbed by the skin, leaving a pleasant velvety afterfeel.

EXAMPLE 28

FINGERNAIL POLISH

In this Example, a fingernail polish remover/conditioner was prepared using the composition of this invention. The composition included components as follows:

|   | Content | % by Weight |
|---|---------|-------------|
| A. | ethyl acetate | 15.00 |
|   | acetone | 74.00 |
|   | Albinco Gel "B"** | 1.00 |
| B. | protein fatty acid condensate | 1.10 |
|   | acetylated lanolin alcohol | 1.00 |
|   | benzoate esters* | 3.00 |
|   | water | 4.00 |

**Carbohydrate based mixed ester-ether gum product of Anheuser-Busch, Inc., St. Louis, Missouri
*Benzoic acid ester of NEODOL 25

In preparing the composition, the ethylacetate and acetone were combined, the Abinco Gel "B" added, and the blend was mixed well for about 40 minutes, to swell the gum. While mixing, the components of group B were added in the order listed. The blend was thereupon mixed for 10 minutes to yield the final product. Such product, when utilized, prevented "whitening" and dryness of the fingers and skin, and provided dry lubrication and a good cosmetic feel and emolliency to the fingers.

EXAMPLE 29

HAIR BRILLIANTINE

In this Example, a hair "brilliantine" was prepared using the ester compositions of this invention. The composition included components as follows:

| Component | % by Weight |
|-----------|-------------|
| Acetulan** | 5.0 |
| Benzoate esters* | 94.5 |
| Fragrance | 0.5 |
| Preservative, color | q.s. |

**Acetylated lanolin alcohol product of Amerchol, Div. of CPC International, Edison, New Jersey 08817
*Benzoic acid ester of NEODOL 25

In preparing the composition, the several components were combined and mixed in the order listed. The resultant product was a non-greasy, easily applied brilliantine, which increased hair gloss and provided a healthy appearance for same, while also making the hair manageable.

EXAMPLE 30A

TOPICAL PHARMACEUTICAL OINTMENT

A. In this Example, a hydrophilic ointment base was prepared—i.e., an oil-in-water emulsion—using the ester compositions of this invention. The base was typical of those used in topical pharmaceutical ointments and included components as follows:

|   | Component | % by Weight |
|---|-----------|-------------|
| A. | stearyl alcohol | 5.00 |
|   | cetyl alcohol | 5.00 |
|   | glyceryl stearate, S.E. | 3.00 |

-continued

|   | Component | % by Weight |
|---|-----------|-------------|
|   | mineral oil | 3.00 |
|   | benzoate esters* | 5.00 |
|   | antioxidant | 0.10 |
|   | Sorbitan oleate emulsifier | 2.00 |
| B. | water | 70.33 |
|   | propylene glycol | 4.00 |
|   | methyl paraben | 0.17 |
|   | propyl paraben | 0.05 |
|   | PEG-40 stearate | 0.75 |
|   | Sta-Sol** | 0.85 |
| C. | Polysorbate 60 | 0.50 |
|   | fragrance | 0.25 |

**Lecithin product of A.E. Staley Mfg. Co., Decatur, Illinois, 62525
*Benzoic acid ester of NEODOL 25

In preparing the composition, the components of group A and the components of group B were separately mixed and heated to 65° C. With stirring, group A was then added to group B and mixed for 15 minutes. The blend was cooled to 35° C. and the group C components were added. The resultant product was a smooth spreading ointment base, which when applied to the skin provided a pleasant emolliency, yet without a greasy feel.

EXAMPLE 30B

In this Example a lipophilic ointment base was prepared—i.e. a water-in-oil emulsion—using the ester composition of this invention. The base was again typical of those used in topical pharmaceutical ointments, and included components as follows

|   | Component | % by wt. |
|---|-----------|----------|
| A. | benzoate esters* | 5.0 |
|   | oleth-2 emulsifier | 5.0 |
|   | propyl paraben | 0.1 |
| B. | methyl paraben | 0.1 |
|   | sorbitol | 5.0 |
|   | water | 84.8 |

*benzoic acid ester of NEODOL 25

In preparing the composition, the components of group A and the components of group B were separately combined and mixed. With stirring, group B was then slowly added to group A—with the stirring rate being increased as the emulsion thickened. The resultant product was again found to be a smooth spreading ointment base, which when applied to the skin provided a pleasant emolliency, without any greasy feel.

EXAMPLE 31

DEODORANT

In this Example, a "personal deodorant" was prepared using the ester compositions of this invention. The composition included components as follows:

| Component | % by Weight IN CONCENTRATE | % by Weight IN CAN |
|-----------|----------------------------|---------------------|
| Triclosan+ | 0.15 | |
| Benzoate esters* | 60.00 | |
| S.D. alcohol, 190 proof | 39.65 | > 70.0 |
| Fragrance | 0.20 | |
| Propellant | — | 30.0 |

+ CTFA designation for Ciba-Geigy preservative
*Benzoic acid ester of NEODOL 35

In preparing the composition, the Triclosan and benzoate ester were combined and mixed well. The alcohol and fragrance were added together and well mixed. The resulting concentrate was added to an aerosol container, and aerosol valve applied, and the container was pressurized with a suitable propellant. The product was tested, and was found to not only be an excellent deodorant, but when sprayed on the skin, provided a dry emolliency, without any feeling of greasiness.

EXAMPLE 32

COLD CREAM

To demonstrate the desired dry lubricating properties of the benzoic acid ester compositions of this invention, a basic cold cream was prepared utilizing 40% mineral oil in one formulation (FORMULATION A) and 20% mineral oil and 20% of the NEODOL 25 benzoates (FORMULATION B). These formulations are listed below:

| BASIC COLD CREAM COMPARISON | | |
|---|---|---|
| | % by wt. | |
| | FORMU-LATION A | FORMU-LATION B |
| A. Water, purified | 43.20 | 43.20 |
| Veegum (Magnesium Aluminum Silicate)* | 1.00 | 1.00 |
| Borax (Sodium Borate) | 0.50 | 0.50 |
| Methyl paraben (methyl p-hydroxbenzoate) | 0.20 | 0.20 |
| B. Light mineral oil, N.F. | 40.00 | 20.00 |
| Beeswax, white, U.S.P. | 10.00 | 10.00 |
| Paraffin wax, 133–135° F. | 5.00 | 5.00 |
| NEODOL 25 benzoate | — | 20.00 |
| C. Fragrance | 0.10 | 0.10 |
| | 100.00 | 100.00 |

*R. T. Vanderbilt Co., Inc., Norwalk, CT 06855

PROCEDURE

1. Rapidly stir water and slowly add Veegum. Stir for 20 minutes then hat to 83°–85° C. while mixing.
2. Add Borax and Methyl paraben and stir.
3. Mix and heat B to 80°–82° C.
4. While B is being mixed, add A.
5. Q.S. with water if necessary.
6. Mix rapidly while cooling to 41°–43° C.
7. Add fragrance, C; mix and cool to 24°–27° C.

A panel was given each formulation to apply to his or her skin and to describe the difference, if any, on the feel on the skin.

The panel selected FORMULATION B as being dry with good emolliency and FORMULATION A as being oily.

The use of the benzoic acid esters of this invention dramatically reduce the greasy sensation when the cold cream is applied to the skin and leaves the skin feeling smooth and dry. Additionally, the esters enhance the cleansing action of the cream.

EXAMPLE 33

COLD CREAM CLEANSER-CONDITIONER

| | % by wt. |
|---|---|
| A. Water, purified | 53.63 |
| Propylene glycol | 4.00 |
| Veegum (Magnesium Aluminum Silicate)[1] | 1.50 |
| B. Cerasynt Q (Glyceryl Stearate, self-emulsifying)[2] | 10.00 |

-continued

| | % by wt. |
|---|---|
| Pluronic F-68 (Poloxamer 188, a block polymer)[3] | 3.00 |
| Mineral Oil, Light N.F. | 14.00 |
| NEODOL 25 benzoate | 9.00 |
| Lanolin Oil | 0.50 |
| Amerchol L-101 (Mineral oil + lanolin alcohol)[4] | 2.50 |
| Hamposyl C (Cocoyl sarcosinate)[5] | 0.50 |
| Methyl paraben (Methyl p-hydroxybenzoate) | 0.15 |
| Antioxidant G-50[6] | 0.05 |
| C. Water | 1.00 |
| Dowicil 200 (Quaternium 15)[7] | 0.12 |
| D. Fragrance | 0.05 |
| | 100.00 |

[1]R. T. Vanderbilt Co., Norwalk, CT 07855
[2]Van Dyk & Co., Belleville, NJ 07109
[3]BASF Wyandotte Corporation, Wyandotte, MI 48902
[4]Amerchol, a unit of CPC Int'l, Edison, NJ 08817
[5]Organic Chemicals div., W.R. Grace & Co., Nashua, NH 03061
[6]Griffith Laboratories, Union City, NJ 07083
[7]Dow Chemical Co., Midland, MI 48640

PROCEDURE

1. Mix A rapidly for 25 minutes and then heat to 71°–73 C.
2. Mix and heat B to 69°–71° C. and add B to A.
3. Continue to mix and cool to 41°–43° C. Combine C and add to cream.
4. Add D. Mix and cool to 20°–23° C.

A light modern cream, balanced for cleansing and emolliency without greasy residue. Wipe on/off; wipe on/wash off, or wipe on/leave on to soften skin and simplify makeup removal.

EXAMPLE 34

LIGHT COLD CREAM

| | % by wt. |
|---|---|
| A. NEODOL 25 benzoate | 10.00 |
| Antioxidant G-50[1] | 0.10 |
| Mineral Oil, light N.F. | 10.00 |
| Cerasynt 945 (Glycerol monostearate)[2] | 7.00 |
| Sorbotex AA (Mineral oil, lanolin alcohol, and glyceryl oleate)[2] | 2.00 |
| Tween 60 (Polysorbate 60)[3] | 0.50 |
| Propyl paraben (Propyl p-hydroybenzoate) | 0.10 |
| Cetyl alcohol | 6.30 |
| B. Water, purified | 55.70 |
| Glycerin | 8.00 |
| Glydant, DMDM Hydantoin, 55% Solution[4] | 0.15 |
| C. Fragrance | 0.15 |

[1]Griffith Laboratories, Union City, NJ 07083
[2]VanDyk & Co., Inc., Belleville, NJ 07109
[3]ICI Americas, Inc., Wilmington, DE 19899
[4]Glyco-Chemicals, Inc., Greenwich, CT 06830

PROCEDURE

1. Mix and heat ingredients A to 61°–63° C.
2. Add to previously mixed ingredients B, mix and heat to 63°–65° C.
3. Mix and cool to 41°–43° C. Add fragrance.
4. Mix and cool to R.T.
5. Twelve to fourteen hours after batch is completed, remix for maximum of physical appearance.

This cream has a smooth dry lubricating feel with improved spreadability.

EXAMPLE 35

BASIC OIL-IN-WATER LOTION

| | | % by wt. |
|---|---|---|
| A. | NEODOL 25 benzoate | 20.20 |
| | Sorbitan stearate (Sorbitan monostearate) | 2.61 |
| B. | Polysorbate 60 (POR (20) sorbitan monostearate) | 0.39 |
| | Water, purified | 75.70 |
| C. | Water, purified | 55.70 |
| | Dowicil 200 (Quaternium-15)[1] | 1.00 |
| | | 100.00 |

[1]Dow Chemical Co., Midland, MI 48640

PROCEDURE

1. Combine, mix and heat A to 61°–63° C.
2. Head B to 63°–65° C.
3. Add A to B with mixing until homogeneous
4. Continue mixing and cool to 41°–43° C.
5. Combine C. Add to lotion and mix.

NOTE: Emulsion may look grainy initially but smoothes out within 24 hours.

An example of a lotion which is non-oily and has good dry emolliency.

EXAMPLE 36

ACID-STABLE OIL-IN-WATER LOTIONS AND CREAMS

| | | % by Weight | | | |
|---|---|---|---|---|---|
| | | A<br>Milk | B<br>Thin<br>Lotion | C<br>Medium<br>Lotion | D<br>Light<br>Cream |
| A. | Cerasynt 945 (mix of glyceryl stearate and POE (23) lauryl ether)[1] | 8.50 | 12.50 | 12.50 | 12.50 |
| | NEODOL 25 benzoate | 4.00 | 6.00 | 6.00 | 6.00 |
| | Amerchol L-101 (mix of mineral oil and lanolin alcohol)[2] | 4.00 | 4.00 | 5.00 | 6.00 |
| | Polysorbate 60 (POE (20) sorbitan monostearate) | 1.75 | 1.75 | 1.75 | 2.00 |
| | Sorbitan Monostearate | 0.75 | 0.75 | 0.75 | 0.75 |
| | Cetyl Alcohol | 1.50 | 2.00 | 2.50 | 2.50 |
| | Antioxidant G-50[3] | 0.04 | 0.04 | 0.04 | 0.04 |
| B. | Water, purified | 70.77 | 64.27 | 62.77 | 61.52 |
| | Propylene Glycol | 8.00 | 8.00 | 8.00 | — |
| | PEG-8 (Polyethylene glycol 400) | — | — | — | 8.00 |
| | Na₂ EDTA (Disodium Edetate) | 0.04 | 0.04 | 0.04 | 0.04 |
| | Hamposyl L-30 (Sodium lauroyl sarcosinate)[4] | 0.50 | 0.50 | 0.50 | 0.50 | ph = 4.5–5.0

[1]Van Dyk & Co., Inc., Belleville, NJ 07109
[2]Amerchol, a Unit of CPC Int'l., Inc., Edison, NJ 08817
[3]Griffith Laboratories, Inc., Union City, NJ 07083
[4]W.R. Grace & Co., Hampshire Div., Nashua, NH 03061

PROCEDURE

1. Mix and heat ingredients A to 62°–64° C.
2. Mix and heat B to 65°–67° C.
3. Add A to B. Mix and cool to 21°–24° C.

All four formulations have a dry lubricating feel. These formulations demonstrate the versatile applications of the benzoate esters of this invention.

EXAMPLE 37

HAND LOTION

| | | % by wt. |
|---|---|---|
| A. | NEODOL 25 benzoate | 12.00 |
| | Unimulse C (Dairy solids co-dried with nonionic and anionic emulsifiers)[1] | 2.00 |
| | Steralchol (Mineral oil and lanolin alcohol)[2] | 3.00 |
| | Fragrance | 0.50 |
| B. | Water, purified | 76.50 |
| | Dowicil 200 (Quaternium-15)[3] | 0.20 |
| | Tetrasodium Edetate | 0.20 |
| C. | Propylene Glycol | 3.30 |
| | Ajidew N-50 (Sodium pyrrolidone carboxylate)[4] | 2.00 |
| | Methyl Paraben (methyl p-hydroxybenzoate) | 0.20 |
| | Propyl Paraben (propyl p-hydroxybenzoate) | 0.10 |

[1]Synfleur-Fidco Co., Monticello, NY 12701
[2]The Lanaetex Products., Inc., Elizabeth, NJ 07206
[3]Dow Chemical Co., Midland, MI 48640
[4]Ajinmoto Company of New York, Inc., New York, NY 10022

PROCEDURE

1. Combine and mix Phase A.
2. Combine and mix Phase B.
3. Stirring, gradually add Phase B to Phase A.
4. Combine and mix Phase C and add Phase C to A & B with high-speed stirring for three to five minutes.

A cold processed oil-in-water lotion containing a milk derived protein and the sodium salt of a natural occurring skin humectant. It also conditions and acts as a moisture trap. The benzoate esters of this invention provide emolliency without an oily feel and ease of emulsification without heating.

EXAMPLE 38

SKIN MOISTURIZER

| | | % by wt. |
|---|---|---|
| A. | Water, purified | 86.10 |
| | Glycerin | 2.00 |
| | Methylparaben | 0.15 |
| | PEG-40 stearate[1] | 0.50 |
| B. | NEODOL 25 benzoate* | 4.00 |
| | Glycerol stearate SE[2] | 2.50 |
| | Cetyl Alcohol | 3.50 |
| | Dimethicone[3] | 1.00 |
| | Propylparaben | 0.50 |
| C. | D & C Green #5, 1% Aq. soln. | 0.10 |
| D. | Fragrance | 0.10 |

[1]Myrj 52S (ICI Americas)
[2]Cerasynt Q (Van Dyk & Co.)
[3]Silicone Fluid SF-96 (General Electric/Silicones)

PROCEDURE

1. Mix and heat A to 65°–67° C.
2. Mix and heat B to 63°–65° C.
3. Add B to A with mixing.
4. Cool to 45° C. with mixing. Add color C.
5. Cool to 40°–43° C. with mixing. Add fragrance D.
6. Mix and cool to 23°–26° C.

This formulation demonstrates a dry velvety feel. A similar formulation without the benzoate is oil and greasy. When isopropyl myristate is substituted for the benzoate, the product is still oily.

EXAMPLE 39

LIGHT BODY LOTION

| | | % by wt. |
|---|---|---|
| A. | NEODOL 25 benzoate | 5.00 |
| | Amerchol L-101 (Mineral oil + lanolin alcohol)[1] | 4.00 |
| | Stearic acid | 2.40 |
| | Cerasynt Q (Glyceryl Stearate, self-emulsifying)[2] | 2.00 |
| | Sesame Oil | 4.40 |
| | Antioxidant G-50[3] | 0.15 |
| | Propyl paraben (propyl p-hydroxybenzoate) | 0.05 |
| B. | Water, purified | 74.95 |
| | Glycerin | 4.50 |
| | TEA, 85% (Triethanolamine) | 1.10 |
| | Methyl paraben (methyl p-hydroxybenzoate) | 0.15 |
| C. | Fragrance(s) | 0.25 |
| D. | D & C Yellow #10, 0.5% aq. soln. | 0.05 |

[1]Amerchol, a unit of CPC Int'l., Inc., Edison, NJ 08817
[2]Van Dyk & Co., Belleville, NJ 07109
[3]Griffith Laboratories, Union City, NJ 07083

PROCEDURE

1. Mix ingredients A and heat to 55° C.
2. Mix B with no heat.
3. Add A to B, mix and heat to 60° C.
4. Mix and cool to below 27° C.

The benzoate eliminates the oil feel of mineral oil and oil and improves spreadability.

EXAMPLE 40

FACIAL CLEANSER EMULSION

| | | % by wt. |
|---|---|---|
| A. | Cerasynt MN (Glycol Stearate SE)[1] | 0.50 |
| | Cetyl alcohol | 0.20 |
| | Stearal alcohol XXX | 0.20 |
| | NEODOL 25 benzoate | 0.60 |
| | PEG 400 diisostearate | 3.50 |
| B. | Hamposyl L-30 (Sodium Lauroyl Sarcosinate)[2] | 10.00 |
| C. | AMINOL LM-5C | 7.00 |
| D. | Methyl paraben | 0.20 |
| | Propyl paraben | 0.05 |
| | Propylene glycol | 9.00 |
| E. | Lactic acid, 85% | 1.20 |
| F. | Water, purified | 67.50 |
| | Disodium EDTA | 0.02 |
| G. | FD&C Green (1% aq. soln.) | 0.03 |

(ph = 4.7-5.1)
[2]Van Dyk & Co., Belleville, NJ 07109
[3]Hampshire Chemical Div., W.R. Grace & Co., Nashua, NH 03060

PROCEDURE

1. Mix and warm A ingredients to 65° C.
2. Add B to A with agitation at 65° C.
3. Add C to above and agitate at 65° C.
4. Mix D to dissolve with slight heat. Add to above mix.
5. Add E to above with agitation. May be diluted with water from F.
6. Mix F and heat to 60° C. Add step 5 mix to the water (F) mix. Agitate and cool to 45° C.
7. Add G to above at 45° C. Mix and cool to R.T.

This formulation demonstrates that even at a low concentration of benzoate in the formulation, the benzoate imparts a dry emollient feel to the skin while enhancing the solubility of facial oils.

EXAMPLE 41

IMPROVED WATER-IN-OIL CLEANSING CREAM

| | | % by wt. |
|---|---|---|
| A. | Beeswax, white | 11.00 |
| | Cetyl alcohol | 2.50 |
| | Cetyl palmitate | 2.20 |
| | Mineral oil, light, NF | 28.00 |
| | NEODOL 25 benzoate | 20.60 |
| | Cerasynt Q (Glyceryl stearate, self-emulsifying)[1] | 0.75 |
| | Propyl paraben (propyl p-hydroxybenzoate) | 0.05 |
| B. | Water, purified | 32.83 |
| | Borax (sodium borate) | 0.75 |
| | Methyl paraben (methyl p-hydroxybenzoate) | 0.15 |
| C. | Water, purified | 1.00 |
| | Dowicil 200 (Quaternium-15)[2] | 0.10 |
| D. | Fragrance | 0.07 |

[1]Van Dyk & Company, Inc., Belleville, NJ 07109
[2]Dow Chemical Co., Midland, MI 48640

PROCEDURE

1. Mix and heat A to 81°-83° C.
2. Mix and heat B to 83°-85° C.
3. Add B to A and mix rapidly. Cool to 55° C.
4. Dissolve C and add to cream.
5. Cool to 40°-42° C. before adding D. May be homogenized at this point.
6. Continue mixing and cool to 24°-28° C.

The benzoates of this invention improve cleansing action while eliminating the greasy feel of the high content of mineral oil. Provide for easy wipe on/off action and dry emolliency. Can be used as a night cream.

EXAMPLE 42

AFTER BATH SPLASH

| | | % by wt. |
|---|---|---|
| A. | S.D. alcohol 39C, 190° proof ethanol | 76.00 |
| B. | NEODOL 25 benzoate | 20.00 |
| C. | Procetyl AWS (PPG-5-Ceteth-20)[1] | 1.30 |
| D. | Glycerin, USP | 1.50 |
| E. | Standamul G-16 (Isocetyl alcohol)[2] | 0.90 |
| F. | Fragrance | 0.30 |

[1]Croda, Incorporated, New York, NY 10010
[2]Henkel, Inc., Fort Lee, NJ 07024

PROCEDURE

1. Mix ingredients in order listed.
2. Agitate batch for about 25 minutes.

A refreshing astringent, non-oiling emollient for application to damp-dry skin, after bath or shower. The benzoate provides for non-oily emolliency in the presence of a high amount of ethanol, generally considered to be drying to the skin.

EXAMPLE 43

AFTER BATH LEMON BODY LOTIONS

| | | % by wt. | |
|---|---|---|---|
| | | FORMULATION A | FORMULATION B |
| A. | Water, purified | 65.75 | 66.55 |
| | Carbopol 941 (Carboxy vinyl polymer)[1] | 0.30 | 0.30 |
| B. | Dry Flo (Aluminum Starch | | |

-continued

|   | % by wt. | |
|---|---|---|
|   | FORMULATION A | FORMULATION B |
| Octenylsuccinate[2] | 5.00 | — |
| Ster-O-Pro (Oat Powder)[3] | — | 4.20 |
| C. SD40/190° Alcohol | 20.00 | 20.00 |
| NEODOL 25 benzoate | 4.00 | 4.00 |
| Solulan 98 (Acetylated ethoxylated lanolin)[4] | 1.00 | 1.00 |
| Alcolec 4135 (lecithin)[5] | 0.50 | 0.50 |
| Propyl paraben (propyl p-hydroxybenzoate) | 0.05 | 0.05 |
| Methyl paraben (methyl p-hydroxybenzoate) | 0.15 | 0.15 |
| D. Water | 2.70 | 2.70 |
| TEA, 85% (Triethanolamine) | 0.30 | 0.30 |
| E. D & C Yellow #5, 0.5% aq. sol. | 0.05 | 0.05 |
| D & C Yellow #10, 0.5% aq. sol. | 0.05 | 0.05 |
| F. Shaw Mudge Lemon #M5405 | 0.05 | 0.05 |
| Perry Bros. Lemon-Musk #72-271 | 0.10 | 0.10 |

[1] B.F. Goodrich Chemical Div., Cleveland, OH 44131
[2] National Starch & Chemical Co., Bridgewater, NJ 08807
[3] Quaker Oats Co., Chicago, IL 60654
[4] Amerchol, a unit of CPC Int'l, Inc., Edison, NJ 08817
[5] American Lecithin Co., Woodside, NY 11377

PROCEDURE

1. Thoroughly disperse Carbopol 941 in water.
2. Add Dry Flo or Ster-O-Pro and mix 25 minutes.
3. Mix TEA in water and add to above; mix for 5 minutes.
4. Combine and mix C and add to above; mix
5. Add color and fragrance and mix for 15 minutes.

A light astringent and emollient hydroalcoholic lotion with a clean, velvety after-feel. An example of a hydroalcohol lotion with a low concentration of benzoate imparting a velvety after-feel.

While the present invention has been particularly set forth in terms of specific embodiments thereof, it will be understood in view of the present disclosure, that numerous variations upon the invention are now enabled to those skilled in the art, which variations reside within the scope of the present teaching. Accordingly, the invention is to be broadly construed, and limited only by the scope and spirit of the claims now appended hereto.

EXAMPLE 44

DUST SUPPRESSANT

In this example a composition in accordance with the invention was used as a means for a dust suppressant in cotton mills. The presence of such dust is regarded by medical authorities as a health hazard and is considered to be a cause of the so-called "brown lung" disease.

In particular, quantities of the ester product of the invention were sprayed on open bales of cotton in the areas where they were open in the factory located near the feed hoppers to reduce dust. The rate of application was ¼% product by weight of the treated cotton. Results on an experimental basis indicated a 50-60% reduction in environmental dust.

These tests were conducted at the U.S.D.A. research facility in Clemsen, So. Carolina.

A further two-week test was conducted at Parkdale Industries in No. Carolina, in which similar quantities of the product were sprayed on open bales of cottom and the reduction of 44% was measured by vertical elutriators.

EXAMPLE 45

ELIMINATION OF SEPARATE SCOURING STEP IN TEXTILE DYEING

The excellent suspending properties of the present invention eliminate the requirement for a separate scouring step in the dyeing of textiles. Mills can dye and scour textiles in the same bath, reducing energy and water requirements for scouring, combining the step of scouring with the step of dyeing.

An ester composition in accordance with the invention was thus mixed with a suitable quantity of emulsifying agents, and added to the dyeing bath on the basis of 2-4% of the weight of the textile to be treated. The textile was immersed in the bath after being fabricated by weaving or knitting. The fabric was found to be effectively dyed without the separate scouring step that has been required in the past. The resultant textile was apparently clean, evenly dyed and soft to the touch.

While the present invention has been particularly set forth in terms of specific embodiments thereof, it will be understood in view of the present disclosure, that numerous variations upon the invention are now enabled to those skilled in the art, which variations reside within the scope of the present teaching. Accordingly, the invention is to be broadly construed, and limited only by the scope and spirit of the claims now appended hereto.

What is claimed is:

1. A substantially pure benzoic acid ester of a mixture of alcohols, wherein said mixture consists essentially of:
    (A) at least one $C_{12}$ or $C_{14}$ primary alcohol,
    (B) at least one $C_{13}$ or $C_{15}$ primary alcohol, wherein the weight ratio of even carbon number alcohols (A) to odd carbon number alcohols (B) is from about 0.25:1 to about 4:1 and at least 70% by weight of each alcohol is linear and substantially all of the remainder of each alcohol is branched at the two carbon position.
2. The composition of claim 1, wherein the weight ratio of (A) to (B) is from about 0.5:1 to about 3:1.
3. The composition of claim 1, wherein the mixture consists essentially of $C_{12}$, $C_{13}$, $C_{14}$ and $C_{15}$ alcohols.
4. The composition of claim 1 or 2, wherein said mixture consists essentially of, by weight, from about 13 to 31% of $C_{12}$ alcohol, about 28 to 44% of $C_{13}$ alcohol, about 17 to 40% of $C_{14}$ alcohol and about 12 to 19% of $C_{15}$ alcohol.
5. The composition of claim 1, wherein the mixture consists essentially of $C_{12}$ and $C_{13}$ alcohols.
6. The composition of claim 1, wherein the mixture consists essentially of $C_{14}$ and $C_{15}$ alcohols.

* * * * *